United States Patent [19]
Van Hartingsveldt et al.

[11] Patent Number: 5,925,515
[45] Date of Patent: Jul. 20, 1999

[54] DIRECT SELECTION OF TRANSFORMANTS ON ACETATE-CONTAINING MEDIA

[75] Inventors: Willem Van Hartingsveldt; Robert Franciscus Maria Van Gorcom, both of Delft; R. J. Gouka, The Hague; Roelof Ary Lans Bovenberg, Rotterdam, all of Netherlands

[73] Assignee: Gist-brocades B.V., Ma Delft, Netherlands

[21] Appl. No.: 07/861,800

[22] PCT Filed: Oct. 15, 1991

[86] PCT No.: PCT/NL91/00203

§ 371 Date: Jun. 11, 1992

§ 102(e) Date: Jun. 11, 1992

[87] PCT Pub. No.: WO92/07079

PCT Pub. Date: Apr. 30, 1992

Related U.S. Application Data

[63] Continuation-in-part of application No. 07/633,378, Dec. 19, 1990, abandoned.

[30] Foreign Application Priority Data

Oct. 15, 1990 [EP] European Pat. Off. .............. 90202754

[51] Int. Cl.⁶ ............................ C12Q 1/68; C12N 15/80
[52] U.S. Cl. ..................... 435/6; 435/69.1; 435/172.3; 435/183; 435/254.11; 435/254.3; 435/254.5; 435/320.1; 536/23.1; 536/23.2; 536/23.7
[58] Field of Search .................. 435/172.3, 320.1, 435/69.1, 252.3, 6, 183, 254.11, 254.3, 254.5; 536/23.1, 23.2, 23.7

[56] References Cited

FOREIGN PATENT DOCUMENTS

| | | |
|---|---|---|
| 260762 | 3/1986 | European Pat. Off. . |
| 215539 | 3/1987 | European Pat. Off. . |
| 225078 | 6/1987 | European Pat. Off. . |
| 235951 | 9/1987 | European Pat. Off. . |
| 240250 | 10/1987 | European Pat. Off. . |

OTHER PUBLICATIONS

Diez et al. Mol. Gen Genet 218:572–576 (1989).
Beri et al., *Curr. Genet.* (1987) 11:639–641.
Kolar et al., *Gene* (1988) 62:127–134.
Stahl et al., *App. Microbiol. Biotechnol.* (1987) 26:237–241.
Picknett et al., *FEMS Microbiol. Lett.* (1989) 60:165–168.
Whitehead et al., *Mol. Gen. Genet.* (1989) 216:408–411.
Picknett et al., *Curr. Genet.* (1987) 12:449–455.
Diez et al., *Curr. Genet.* (1987) 12:277–282.
O'Sullivan et al., *J. Gen. Microbiol.* (1973) 76:65–75.
Sandeman et al., *Mol. Gen. Genet.* (1989) 218:87–92.
Thomas et al., *Molec. Microbiol.* (1988) 2:599–606.
Connerton et al., *Molec. Microbiol.* (1990) 4:451–460.
Hargreaves et al., *J. Gen. Microbiol.* (1989) 135:2675–2678.
Apirion, *Nature* (1962) 195:959–961.
Casselton et al., *Mol. Gen. Genet.* (1974) 132:255–264.
Mellon et al., *Int. Congr. Microbiol* (1987) 14 Meet., 145.

*Primary Examiner*—John L. LeGuyader
*Attorney, Agent, or Firm*—Morrison & Foerster LLP

[57] ABSTRACT

A transformant selection system has been developed, particularly for a β-lactam producing strain, more particularly for *P. chrysogenum*, by the complementation of a mutation of said β-lactam producing strain by a homologous selection marker without interfering with β-lactam biosynthesis. Particularly, in applying said transformant selection system a positive selection agent, for instance fluoroacetate is used for the isolation of fac mutants of said strain, particularly of said β-lactam producing strain. Furthermore, a gene entitled facA has been isolated from *P. chrysogenum*.

27 Claims, 2 Drawing Sheets

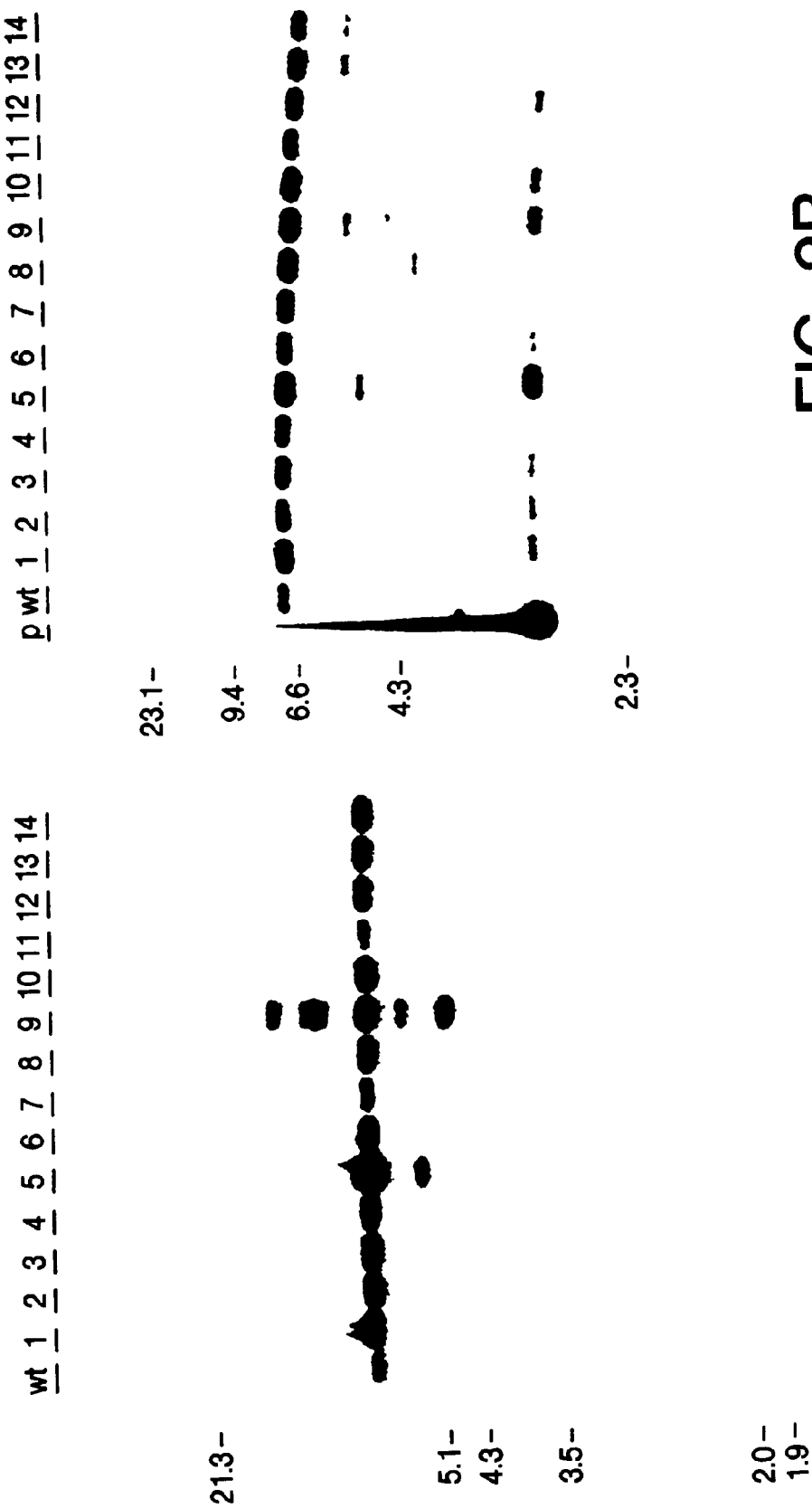

```
                         SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
             (A) LENGTH: 4652 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Penicillium chrysogenum (vii) IMMEDIATE SOURCE:
             (B) CLONE: pPC2-3

(ix) FEATURE:
             (A) NAME/KEY: exon
             (B) LOCATION: 1781..1819

(ix) FEATURE:
             (A) NAME/KEY: intron
             (B) LOCATION: 1820..1904

(ix) FEATURE:
             (A) NAME/KEY: exon
             (B) LOCATION: 1905..3149

(ix) FEATURE:
             (A) NAME/KEY: intron
             (B) LOCATION: 3150..3207

(ix) FEATURE:
             (A) NAME/KEY: exon
             (B) LOCATION: 3208..3468

(ix) FEATURE:
             (A) NAME/KEY: intron
             (B) LOCATION: 3469..3519

(ix) FEATURE:
             (A) NAME/KEY: exon
             (B) LOCATION: 3520..3648

(ix) FEATURE:
             (A) NAME/KEY: intron
             (B) LOCATION: 3649..3709

(ix) FEATURE:
             (A) NAME/KEY: exon
             (B) LOCATION: 3710..3981

(ix) FEATURE:
             (A) NAME/KEY: intron
             (B) LOCATION: 3982..4057

(ix) FEATURE:
```

(A) NAME/KEY: exon
            (B) LOCATION: 4058..4117

(ix) FEATURE:
            (A) NAME/KEY: CDS
            (B) LOCATION: join (1781..1819, 1905..3149, 3208..3468,
                    3520..3648, 3710..3981, 4058..4117)
            (D) OTHER INFORMATION: /codon_start= 1781 /gene= "facA"

(xi) SEQUENCE DESCRIPTION: SEQ ID NO:1:

```
TCTAGACAAA AGGAACGAGA ACTAAAGGAT GCATCCGCCT GTTATCAAAC ATATGATGTG      60

GTCATGACGG CCCTTGTTCC TAAACTTCGT CCTGCAAGAT TACTTGATCC GACCCTTTTT     120

CGACTCTTCC ACTACTGTCA CACAACTTGG AGAGATTCGG CTGTCGCTGT CCGCCAAGAG     180

TTAATTGAGC TTTCAGCTCG CTGGGCGGAA CTGGGGCTAG AGGGCTCATG TCCATATTCT     240

CCCACAGAAG CGGAATTGAA ACAGCACGCT CGAGACTATG AAGATTTTGA GGCTGTTCAA     300

GCACTCAAGT CATGGCTAAG GGACAACCTT GATACAAATT CTGACGGGTG GATCTCGAGT     360

GATGCGTGGG ACGCTGCGAG GGTAGCTCAT CGCGCAGCGT ATGATGAATG GATACAGACT     420

GCCAAAGAAG CCGAGTCCCG TGGCGAAGAC ATGACAGTAG CGAAGGCGGA CAAGATGTGG     480

CCATTTGATG CTAGATAGGA ACTAGGGAGA GGTAATCAAA ATAGCCAGCT GGTCTCTGTC     540

TCTAGGGTCT AGTCTAAACC CAGGCCCTGC CCTTACGTTA GCTTTTCGAC AGGATATGAC     600

GGCCTGATGT TTGTTTCTGC CTGGCTAGGC AATTTTTAAG TAGATCTCGG CTTTGGGTGC     660

GTAGCTTCTG GGAACTTGGT TGGCTCCTCT ACGTCTGAAC AGCTCCTTGG CTGTTGTAGA     720

TGTCGTAGCA GTATATTCAA CCGTACAATA TTTACAATAG TAGTCCAAAG GGTCTCGAGC     780

TTAATGATAC TCCGGCCCCG TCTAAAAGTC ATGTGGTCCA CGCGTTAGCG CGCCGTTAGT     840

CTAAGTATAC GACATATGTA CGACAGACAA GGCCACATGG TGAATTTAGC GCAGGTGTGA     900

CTTTAAGTGG ACCGGCACTG GACGGGTTTG GCGCGAAATA CAGTGCTTTT CTCAACATGT     960

TAACTCTGTA CATCTCCGGC CCTTCCCCCG TGGAATGGGA ATTTTCTTGT ACAATATATG    1020

TTTTGTTGGG ACATTGAGCA AAGAATGGAG TAAACGCGGT CTTTTCTCGG GCCTCTTTCC    1080

TCTGCGTTAA AAATTGGCGG GGCTCGAAGA TACGCTTGTA TTGAAACTGG CTTCTCCCCT    1140

GATCCGCGAC CCCGGACCTT GGCTGAAGTA CCTAGGTTGT GTTGGACTCG GACAAAGGGT    1200

TCAACGAGAA CAACTGGGCT GTGGTCGGTT AAACTTGGCG TTTCTTCCCG ACTATAAACG    1260

CGCCAATGAG GGGACCTGAT CTGAGTCGAA ATCTTTGGAG GGGTAAGCTT ACCCCGGAGC    1320

AACGGAAAGA ACCCCGCAT GGCCGAACCC AAACTCGTAT GGGACAAGGC AATTTACTGA    1380

AATTTACTGA AATTTACTGA ATTGGACCGT ATTCGGAATG TATCTTATTC CTGATTCGGA    1440

GATGAGAGTG GATCGTCCGA ATGTCCAATG CACAATGTAC TTTCTCTAGG CCGTCTGCGG    1500

CTAGCGAGAC AGCCGGAGTT GGGTAGTTTG AAGTGGTATT GTAACTTATT GTAATTTATT    1560

GTAAGGGGCA CGGACCACTG ATGAAAAGGG AAGTGGCACA TCCTCCCGGG ACAGCTGGAC    1620

TACTAATATT GTCGCGAGTC CCCCCTCCTT GAGTTTCTTT TTCTCTTTCT CTTCTCTAAT    1680

ATCTTCTCTA ATTGCTATAC ATACCCTGTT TGATCATTAC TCTTAGTATA TTATATAGTT    1740

CATCCCCCAC ATTTATTATT CCCATTGGAC TACCGCAATC ATG TCG GAC GGC CCA     1795
                                               Met Ser Asp Gly Pro
                                                 1               5

ATT CAG CCT CCC AAG CCC GCA GTG GTAAGAATCA CCGACCTCCA GACCGAGATG     1849
Ile Gln Pro Pro Lys Pro Ala Val
                         10

ACCAGACCCG TGTCGCACTG GTGACCGAAG TATCATGGGC TAACTGGTGA TATAG GTG    1907
                                                                Val
```

| | | | | | | | | | | | | | | | |
|---|---|---|---|---|---|---|---|---|---|---|---|---|---|---|---|
| CAT | GAG | GCA | CAC | GAG | GTC | GAC | ACT | TTC | CAC | GTC | CCC | AAG | GCG | TTC | CAC | 1955 |
| His | Glu | Ala | His | Glu | Val | Asp | Thr | Phe | His | Val | Pro | Lys | Ala | Phe | His | |
| 15 | | | | 20 | | | | 25 | | | | 30 | | | | |

| | | | | | | | | | | | | | | | | |
|---|---|---|---|---|---|---|---|---|---|---|---|---|---|---|---|---|
| GAT | AAG | CAC | CCC | TCC | GGC | ACT | CAC | ATC | AAG | GAC | ATT | GAG | GAG | TAC | AAG | 2003 |
| Asp | Lys | His | Pro | Ser | Gly | Thr | His | Ile | Lys | Asp | Ile | Glu | Glu | Tyr | Lys | |
| | | | 35 | | | | | 40 | | | | | 45 | | | |

| | | | | | | | | | | | | | | | | |
|---|---|---|---|---|---|---|---|---|---|---|---|---|---|---|---|---|
| AAG | CTT | TAC | GAA | GAA | TCA | ATC | AAG | AGC | CCC | GAC | ACC | TTC | TGG | GCA | CGC | 2051 |
| Lys | Leu | Tyr | Glu | Glu | Ser | Ile | Lys | Ser | Pro | Asp | Thr | Phe | Trp | Ala | Arg | |
| | | | 50 | | | | | 55 | | | | | 60 | | | |

| | | | | | | | | | | | | | | | | |
|---|---|---|---|---|---|---|---|---|---|---|---|---|---|---|---|---|
| ATG | GCC | CGC | GAG | CTC | CTC | ACA | TTT | GAC | AAG | GAC | TTT | GAA | ACC | ACA | CAT | 2099 |
| Met | Ala | Arg | Glu | Leu | Leu | Thr | Phe | Asp | Lys | Asp | Phe | Glu | Thr | Thr | His | |
| | | 65 | | | | | 70 | | | | | 75 | | | | |

| | | | | | | | | | | | | | | | | |
|---|---|---|---|---|---|---|---|---|---|---|---|---|---|---|---|---|
| CAC | GGC | TCG | TTT | GAG | AAC | GGC | GAC | AAT | GCC | TGG | TTC | GTC | GAG | GGT | CGG | 2147 |
| His | Gly | Ser | Phe | Glu | Asn | Gly | Asp | Asn | Ala | Trp | Phe | Val | Glu | Gly | Arg | |
| | 80 | | | | | 85 | | | | | 90 | | | | | |

| | | | | | | | | | | | | | | | | |
|---|---|---|---|---|---|---|---|---|---|---|---|---|---|---|---|---|
| TTG | AAC | GCA | TCG | TTC | AAC | TGT | GTC | GAT | CGC | CAT | GCC | CTC | AAG | AAC | CCA | 2195 |
| Leu | Asn | Ala | Ser | Phe | Asn | Cys | Val | Asp | Arg | His | Ala | Leu | Lys | Asn | Pro | |
| 95 | | | | | 100 | | | | | 105 | | | | | 110 | |

| | | | | | | | | | | | | | | | | |
|---|---|---|---|---|---|---|---|---|---|---|---|---|---|---|---|---|
| GAT | AAG | GTC | GCC | ATT | ATT | TAT | GAG | GCC | GAC | GAG | CCC | AAC | GAG | GGC | CGT | 2243 |
| Asp | Lys | Val | Ala | Ile | Ile | Tyr | Glu | Ala | Asp | Glu | Pro | Asn | Glu | Gly | Arg | |
| | | | | 115 | | | | | 120 | | | | | 125 | | |

| | | | | | | | | | | | | | | | | |
|---|---|---|---|---|---|---|---|---|---|---|---|---|---|---|---|---|
| AAG | ATC | ACC | TAC | GGA | GAG | CTG | ATG | CGC | GAG | GTG | TCC | CGG | GTT | GCC | TGG | 2291 |
| Lys | Ile | Thr | Tyr | Gly | Glu | Leu | Met | Arg | Glu | Val | Ser | Arg | Val | Ala | Trp | |
| | | | 130 | | | | | 135 | | | | | 140 | | | |

| | | | | | | | | | | | | | | | | |
|---|---|---|---|---|---|---|---|---|---|---|---|---|---|---|---|---|
| ACT | CTG | AAG | GAG | CGT | GGC | GTC | AAG | AAG | GGC | GAC | ACG | GTC | GGT | ATC | TAC | 2339 |
| Thr | Leu | Lys | Glu | Arg | Gly | Val | Lys | Lys | Gly | Asp | Thr | Val | Gly | Ile | Tyr | |
| | | 145 | | | | | 150 | | | | | 155 | | | | |

| | | | | | | | | | | | | | | | | |
|---|---|---|---|---|---|---|---|---|---|---|---|---|---|---|---|---|
| CTG | CCC | ATG | ATT | CCC | GAG | GCC | GTA | ATC | GCT | TTC | CTG | GCT | TGC | TCG | CGT | 2387 |
| Leu | Pro | Met | Ile | Pro | Glu | Ala | Val | Ile | Ala | Phe | Leu | Ala | Cys | Ser | Arg | |
| | 160 | | | | | 165 | | | | | 170 | | | | | |

| | | | | | | | | | | | | | | | | |
|---|---|---|---|---|---|---|---|---|---|---|---|---|---|---|---|---|
| ATT | GGT | GCC | GTG | CAC | TCC | GTT | GTC | TTC | GCT | GGT | TTC | TCT | TCC | GAC | TCC | 2435 |
| Ile | Gly | Ala | Val | His | Ser | Val | Val | Phe | Ala | Gly | Phe | Ser | Ser | Asp | Ser | |
| 175 | | | | | 180 | | | | | 185 | | | | | 190 | |

| | | | | | | | | | | | | | | | | |
|---|---|---|---|---|---|---|---|---|---|---|---|---|---|---|---|---|
| CTC | CGG | GAC | CGT | GTC | CTG | GAC | GCC | TCC | TCC | AAG | GTC | ATC | ATT | ACC | TCC | 2483 |
| Leu | Arg | Asp | Arg | Val | Leu | Asp | Ala | Ser | Ser | Lys | Val | Ile | Ile | Thr | Ser | |
| | | | | 195 | | | | | 200 | | | | | 205 | | |

| | | | | | | | | | | | | | | | | |
|---|---|---|---|---|---|---|---|---|---|---|---|---|---|---|---|---|
| GAC | GAG | GGC | AAG | CGC | GGT | GGC | AAG | ATC | ATT | GGC | ACT | AAG | AAG | ATT | GTG | 2531 |
| Asp | Glu | Gly | Lys | Arg | Gly | Gly | Lys | Ile | Ile | Gly | Thr | Lys | Lys | Ile | Val | |
| | | | 210 | | | | | 215 | | | | | 220 | | | |

| | | | | | | | | | | | | | | | | |
|---|---|---|---|---|---|---|---|---|---|---|---|---|---|---|---|---|
| GAC | GAG | GCC | ATG | AAG | CAG | TGC | CCC | GAT | GTC | GAC | ACC | GTG | CTG | GTG | TAC | 2579 |
| Asp | Glu | Ala | Met | Lys | Gln | Cys | Pro | Asp | Val | Asp | Thr | Val | Leu | Val | Tyr | |
| | | 225 | | | | | 230 | | | | | 235 | | | | |

| | | | | | | | | | | | | | | | | |
|---|---|---|---|---|---|---|---|---|---|---|---|---|---|---|---|---|
| AAG | CGC | ACC | GGT | GCC | GAG | GTG | CCC | TGG | ACC | GCT | GGC | CGT | GAC | ATT | TGG | 2627 |
| Lys | Arg | Thr | Gly | Ala | Glu | Val | Pro | Trp | Thr | Ala | Gly | Arg | Asp | Ile | Trp | |
| | 240 | | | | | 245 | | | | | 250 | | | | | |

| | | | | | | | | | | | | | | | | |
|---|---|---|---|---|---|---|---|---|---|---|---|---|---|---|---|---|
| TGG | CAC | GAG | GAG | GTC | GAG | AAG | TAC | CCC | AAC | TAC | CTC | GCC | CCT | GAG | TCG | 2675 |
| Trp | His | Glu | Glu | Val | Glu | Lys | Tyr | Pro | Asn | Tyr | Leu | Ala | Pro | Glu | Ser | |
| 255 | | | | | 260 | | | | | 265 | | | | | 270 | |

| | | | | | | | | | | | | | | | | |
|---|---|---|---|---|---|---|---|---|---|---|---|---|---|---|---|---|
| GTC | AGC | TCC | GAG | GAT | CCT | CTC | TTC | CTG | TTG | TAC | ACC | TCC | GGT | TCC | ACC | 2723 |
| Val | Ser | Ser | Glu | Asp | Pro | Leu | Phe | Leu | Leu | Tyr | Thr | Ser | Gly | Ser | Thr | |
| | | | | 275 | | | | | 280 | | | | | 285 | | |

| | | | | | | | | | | | | | | | | |
|---|---|---|---|---|---|---|---|---|---|---|---|---|---|---|---|---|
| GGT | AAG | CCC | AAG | GGT | GTT | ATG | CAC | ACC | ACT | GCC | GGT | TAC | CTG | CTC | GGT | 2771 |
| Gly | Lys | Pro | Lys | Gly | Val | Met | His | Thr | Thr | Ala | Gly | Tyr | Leu | Leu | Gly | |
| | | | 290 | | | | | 295 | | | | | 300 | | | |

| | | | | | | | | | | | | | | | | |
|---|---|---|---|---|---|---|---|---|---|---|---|---|---|---|---|---|
| GCG | GCC | ATG | ACT | GGA | AAG | TAC | GTG | TTT | GAT | ATC | CAC | GAC | GAT | GAT | CGC | 2819 |
| Ala | Ala | Met | Thr | Gly | Lys | Tyr | Val | Phe | Asp | Ile | His | Asp | Asp | Asp | Arg | |
| | | 305 | | | | | 310 | | | | | 315 | | | | |

| | | | | | | | | | | | | | | | | |
|---|---|---|---|---|---|---|---|---|---|---|---|---|---|---|---|---|
| TAC | TTC | TGC | GGT | GGT | GAT | GTC | GGT | TGG | ATT | ACA | GGT | CAC | ACC | TAT | GTC | 2867 |
| Tyr | Phe | Cys | Gly | Gly | Asp | Val | Gly | Trp | Ile | Thr | Gly | His | Thr | Tyr | Val | |
| | 320 | | | | | 325 | | | | | 330 | | | | | |

-continued

```
GTG TAC GCC CCT CTA TTG CTT GGC TGC GCC ACC GTC GTG TTC GAG AGT         2915
Val Tyr Ala Pro Leu Leu Leu Gly Cys Ala Thr Val Val Phe Glu Ser
335             340                 345                 350

ACC CCC GCC TAC CCT AAC TTC TCG CGC TAC TGG GAT GTC ATT GAC AAG         2963
Thr Pro Ala Tyr Pro Asn Phe Ser Arg Tyr Trp Asp Val Ile Asp Lys
                355                 360                 365

CAC GAC GTC ACA CAA TTC TAC GTT GCA CCC ACC GCT CTG CGT CTG CTG         3011
His Asp Val Thr Gln Phe Tyr Val Ala Pro Thr Ala Leu Arg Leu Leu
            370                 375                 380

AAG CGC GCT GGA GAT GAG CAC ATT CAC CAC AAG ATG CAC AGT CTG CGT         3059
Lys Arg Ala Gly Asp Glu His Ile His His Lys Met His Ser Leu Arg
        385                 390                 395

ATT CTT GGC TCC GTC GGA GAG CCC ATT GCC GCG GAA GTC TGG AAG TGG         3107
Ile Leu Gly Ser Val Gly Glu Pro Ile Ala Ala Glu Val Trp Lys Trp
    400                 405                 410

TAC TTC GAG TGT GTT GGC AAG GAG GAA GCT CAC ATC TGC GAC                 3149
Tyr Phe Glu Cys Val Gly Lys Glu Glu Ala His Ile Cys Asp
415                 420                 425

GTTCGTTCCC CCTTACCCTT GGACCTTTTG GAATAACTTC TAATTTTTGG ATCTGTAG         3207

ACA TAC TGG CAA ACC GAG ACC GGC TCA CAT GTC ATC ACC CCT CTC GGC         3255
Thr Tyr Trp Gln Thr Glu Thr Gly Ser His Val Ile Thr Pro Leu Gly
    430                 435                 440

GGT ATC ACC CCC ACC AAG CCC GGC AGT GCC TCC CTA CCC TTC TTC GGT         3303
Gly Ile Thr Pro Thr Lys Pro Gly Ser Ala Ser Leu Pro Phe Phe Gly
445                 450                 455                 460

ATC GAG CCT GCC ATT ATC GAC CCC GTC TCC GGA GAG GAG ATT GTC GGC         3351
Ile Glu Pro Ala Ile Ile Asp Pro Val Ser Gly Glu Glu Ile Val Gly
                465                 470                 475

AAT GAT GTC GAG GGT GTT TTG GCC TTC AAG CAG CCG TGG CCC AGC ATG         3399
Asn Asp Val Glu Gly Val Leu Ala Phe Lys Gln Pro Trp Pro Ser Met
            480                 485                 490

GCC CGC ACC GTG TGG GGT GCC CAC AAG CGT TAC ATG GAC ACT TAC TTG         3447
Ala Arg Thr Val Trp Gly Ala His Lys Arg Tyr Met Asp Thr Tyr Leu
        495                 500                 505

AAC GTG TAC AAG GGT TAC TAC GTAAGACGCT TCGCAGCCTG CCTTGCAGGG            3498
Asn Val Tyr Lys Gly Tyr Tyr
    510                 515

TTGATACTAA CTCATATATA G TTC ACC GGA GAT GGT GCT GGC CGT GAC CAC         3549
                        Phe Thr Gly Asp Gly Ala Gly Arg Asp His
                                        520                 525

GAC GGC TAT TAC TGG ATC CGC GGT CGT GTT GAC GAT GTC GTC AAC GTT         3597
Asp Gly Tyr Tyr Trp Ile Arg Gly Arg Val Asp Asp Val Val Asn Val
                530                 535                 540

TCT GGA CAC CGT CTG TCC ACC GCT GAG ATC GAG GCC GCT CTT CTC GAG         3645
Ser Gly His Arg Leu Ser Thr Ala Glu Ile Glu Ala Ala Leu Leu Glu
            545                 550                 555

CAC  C GTAAGTCCAA CCACAGTATC TGCCAAAAAT TGCAACTGAG CCCAAACTAA           3699
His

CTATGAACAG  CT TCC GTT GCC GAG GCT GCT GTC GTT GGT ATT GCC GAC          3747
            Pro Ser Val Ala Glu Ala Ala Val Val Gly Ile Ala Asp
                560                 565                 570

GAG CTG ACC GGT CAG GCT GTC AAT GCC TTT GTC TCT CTC AAG GAG GGC         3795
Glu Leu Thr Gly Gln Ala Val Asn Ala Phe Val Ser Leu Lys Glu Gly
        575                 580                 585

AAG CCC ACA GAA CAG ATC AGC AAG GAC CTT GCA ATG CAA GTT CGC AAG         3843
Lys Pro Thr Glu Gln Ile Ser Lys Asp Leu Ala Met Gln Val Arg Lys
    590                 595                 600

TCC ATT GGT CCC TTC GCC GCC CCC AAG GCT GTC TTC GTC GTG GAT GAC         3891
Ser Ile Gly Pro Phe Ala Ala Pro Lys Ala Val Phe Val Val Asp Asp
605                 610                 615
```

-continued

```
CTC CCC AAG ACC CGC AGT GGC AAG ATC ATG CGC CGA ATC CTC CGG AAG      3939
Leu Pro Lys Thr Arg Ser Gly Lys Ile Met Arg Arg Ile Leu Arg Lys
620                 625                 630                 635

ATT CTC AGT GGC GAG GAG GAC AGC CTC GGT GAT ACA TCA ACG              3981
Ile Leu Ser Gly Glu Glu Asp Ser Leu Gly Asp Thr Ser Thr
                640                 645

GTAAGCATCA TCTCTCAGCA AGATAGTACC CGCAATCGTA TCGTCCGAAC AATAGCTAAC    4041

GAAATATTCT TCACAG CTC TCC GAC CCC AGT GTC GTG GAC AAG ATC ATA        4090
               Leu Ser Asp Pro Ser Val Val Asp Lys Ile Ile
               650                 655                 660

GAA ACC GTC CAC AGT GCT CGC CAG AAG TAAAGTGAAA GTCTATGAAT            4137
Glu Thr Val His Ser Ala Arg Gln Lys
                665                 670

ATGATGATAA TGACGTCGGA GAGCAAAATT TCTGGTGAAT TTTGGAAGTA GTATGATGGT    4197

CCTCTGCGGA TCATACGCCC TCGACCTCGG TCCACTTGGT TCATGCTGGA ATCGGACTTG    4257

ACCATGCGGG TGGTTTTCTT TTCTTTTCTT TTTTTGGCCG GTTTTCAGAA TCACTGCTTG    4317

TACTTGAGAT TCCCTTGGCT CGCTCAGAAG CGATTTGAAT AGTATTATTT TTTGCCTTCT    4377

TGTATACTTC GGCTCTCTCC TTTGACTCAT CAATATGAAT CGTACCTAGG TATAAGAGCA    4437

TCTTTACGGG TGGAGCCATT GACGGAACTC CATGACGCCG TTGAATGCGC CTTGAGCTAC    4497

TTATAGGGGG CCGGGGGATG TGGTAGAAGG CGATGGATCA TGACTTGAAA CCATACAGAT    4557

GCTGGTGCAG GACTGCACTG GGTTCCCGCG CGTATGCTTC TAATATAAAC GTTCTGTGAC    4617

GCATCTTTTC AATTCTGCGG AAGGGTCAAG AATTC                               4652
```

(2) INFORMATION FOR SEQ ID NO:2:

(i) SEQUENCE CHARACTERISTICS:
        (A) LENGTH: 669 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Asp Gly Pro Ile Gln Pro Pro Lys Pro Ala Val Val His Glu
1               5                   10                  15

Ala His Glu Val Asp Thr Phe His Val Pro Lys Ala Phe His Asp Lys
            20                  25                  30

His Pro Ser Gly Thr His Ile Lys Asp Ile Glu Glu Tyr Lys Lys Leu
        35                  40                  45

Tyr Glu Glu Ser Ile Lys Ser Pro Asp Thr Phe Trp Ala Arg Met Ala
    50                  55                  60

Arg Glu Leu Leu Thr Phe Asp Lys Asp Phe Glu Thr Thr His His Gly
65                  70                  75                  80

Ser Phe Glu Asn Gly Asp Asn Ala Trp Phe Val Glu Gly Arg Leu Asn
                85                  90                  95

Ala Ser Phe Asn Cys Val Asp Arg His Ala Leu Lys Asn Pro Asp Lys
            100                 105                 110

Val Ala Ile Ile Tyr Glu Ala Asp Glu Pro Asn Glu Gly Arg Lys Ile
        115                 120                 125

Thr Tyr Gly Glu Leu Met Arg Glu Val Ser Arg Val Ala Trp Thr Leu
    130                 135                 140

Lys Glu Arg Gly Val Lys Lys Gly Asp Thr Val Gly Ile Tyr Leu Pro
145                 150                 155                 160

Met Ile Pro Glu Ala Val Ile Ala Phe Leu Ala Cys Ser Arg Ile Gly
```

```
                    165                 170                 175
Ala Val His Ser Val Val Phe Ala Gly Phe Ser Asp Ser Leu Arg
                180                 185                 190
Asp Arg Val Leu Asp Ala Ser Ser Lys Val Ile Ile Thr Ser Asp Glu
            195                 200                 205
Gly Lys Arg Gly Gly Lys Ile Ile Gly Thr Lys Lys Ile Val Asp Glu
        210                 215                 220
Ala Met Lys Gln Cys Pro Asp Val Asp Thr Val Leu Val Tyr Lys Arg
225                 230                 235                 240
Thr Gly Ala Glu Val Pro Trp Thr Ala Gly Arg Asp Ile Trp Trp His
                245                 250                 255
Glu Glu Val Glu Lys Tyr Pro Asn Tyr Leu Ala Pro Glu Ser Val Ser
                260                 265                 270
Ser Glu Asp Pro Leu Phe Leu Leu Tyr Thr Ser Gly Ser Thr Gly Lys
            275                 280                 285
Pro Lys Gly Val Met His Thr Thr Ala Gly Tyr Leu Leu Gly Ala Ala
        290                 295                 300
Met Thr Gly Lys Tyr Val Phe Asp Ile His Asp Asp Arg Tyr Phe
305                 310                 315                 320
Cys Gly Gly Asp Val Gly Trp Ile Thr Gly His Thr Tyr Val Val Tyr
                325                 330                 335
Ala Pro Leu Leu Leu Gly Cys Ala Thr Val Val Phe Glu Ser Thr Pro
            340                 345                 350
Ala Tyr Pro Asn Phe Ser Arg Tyr Trp Asp Val Ile Asp Lys His Asp
            355                 360                 365
Val Thr Gln Phe Tyr Val Ala Pro Thr Ala Leu Arg Leu Leu Lys Arg
        370                 375                 380
Ala Gly Asp Glu His Ile His His Lys Met His Ser Leu Arg Ile Leu
385                 390                 395                 400
Gly Ser Val Gly Glu Pro Ile Ala Ala Glu Val Trp Lys Trp Tyr Phe
                405                 410                 415
Glu Cys Val Gly Lys Glu Glu Ala His Ile Cys Asp Thr Tyr Trp Gln
                420                 425                 430
Thr Glu Thr Gly Ser His Val Ile Thr Pro Leu Gly Gly Ile Thr Pro
            435                 440                 445
Thr Lys Pro Gly Ser Ala Ser Leu Pro Phe Phe Gly Ile Glu Pro Ala
450                 455                 460
Ile Ile Asp Pro Val Ser Gly Glu Glu Ile Val Gly Asn Asp Val Glu
465                 470                 475                 480
Gly Val Leu Ala Phe Lys Gln Pro Trp Pro Ser Met Ala Arg Thr Val
                485                 490                 495
Trp Gly Ala His Lys Arg Tyr Met Asp Thr Tyr Leu Asn Val Tyr Lys
                500                 505                 510
Gly Tyr Tyr Phe Thr Gly Asp Gly Ala Gly Arg Asp His Asp Gly Tyr
            515                 520                 525
Tyr Trp Ile Arg Gly Arg Val Asp Asp Val Val Asn Val Ser Gly His
        530                 535                 540
Arg Leu Ser Thr Ala Glu Ile Glu Ala Leu Leu Glu His Pro Ser
545                 550                 555                 560
Val Ala Glu Ala Ala Val Val Gly Ile Ala Asp Glu Leu Thr Gly Gln
                565                 570                 575
Ala Val Asn Ala Phe Val Ser Leu Lys Glu Gly Lys Pro Thr Glu Gln
            580                 585                 590
```

```
Ile Ser Lys Asp Leu Ala Met Gln Val Arg Lys Ser Ile Gly Pro Phe
        595                 600             605

Ala Ala Pro Lys Ala Val Phe Val Val Asp Asp Leu Pro Lys Thr Arg
        610             615             620

Ser Gly Lys Ile Met Arg Arg Ile Leu Arg Lys Ile Leu Ser Gly Glu
625             630                 635                 640

Glu Asp Ser Leu Gly Asp Thr Ser Thr Leu Arg Pro Gln Cys Arg Gly
            645                 650                 655

Gln Asp His Arg Asn Arg Pro Gln Cys Ser Pro Glu Val
            660             665
```

DIRECT SELECTION OF TRANSFORMANTS ON ACETATE-CONTAINING MEDIA

This application is a 371 of PCT/NL91/00203, Oct. 15, 1991, and a CIP of U.S. application Ser. No. 07/633,371, filed Dec. 19, 1990, now abandoned.

The present invention relates to a transformant selection system, particularly for a strain of fungus, more particularly *Penicillium chrysogenum*.

Furthermore, this invention relates to a transformant selection marker, viz. the acetyl-CoA synthetase (facA) gene, isolated from *Penicillium chrysogenum*.

The filamentous fungus *Penicillium chrysogenum* is the most applied producer of the β-lactam compounds penicillin G and penicillin V. Penicillins G/V are used as antibiotics themselves or they are chemically converted into semi-synthetic β-lactams. *P. chrysogenum* has a long record of industrial application. Since the second world war it has been the microorganism of choice for large scale production of penicillins all over the world. Over the years significant improvements have been made in the yield of the penicillin production process, both by strain improvement and by process development. Strain improvement has been pursued by the application of random mutagenesis by chemical and physical means as well as by targeted mutagenesis of key enzymes in metabolic pathways connected to penicillin biosynthesis, followed by extensive selections for strains with increased penicillin titers. For reviews see for example Hersbach, G. J. M., Van der Beek, C. P. and Van Dijck, P. W. M., "The Penicillins: Properties, Biosynthesis and Fermentation" in Biotechnology of Industrial Antibiotics, E. van Damme (ed), Marcel Dekker (NY), 1984 and Rowlands, R. T., Enzyme Microb. Technol. 6, 1984, 3–10 and 290–300.

A novel approach to strain improvement has become possible with the development of recombinant DNA technology. Prerequisites for the application of recombinant DNA techniques to any organism or cell-line, are the availability of a gene transfer and a selection or detection system, which permits the identification of the usually small number of recombinant DNA containing transformed cells, in a vast majority of non-transformed cells. The development of efficient gene transfer and selection systems for β-lactam producing industrial strains, particularly for *P. chrysogenum* is very difficult for two major reasons. First of all, it is a common observation that β-lactam producing industrial strains are by far more difficult to transform than wild type or laboratory strains (Ingolia & Queener, Med. Res. Rev. 9, 1989, 245–264). The feature of impaired transformation of industrial strains might be related to the extensive mutagenesis of these strains. For example, mutations affecting the composition and/or assembly of the cell membrane or the cell wall are likely to accumulate in industrial strains leading to changes in morphology in the course of a strain improvement program. (Lein, in: Overproduction of Microbial Metabolites, Vanek and Hostálek (eds), 1986, Butterworth Publishers, 105–139). These morphological changes might for instance affect the generation of protoplasts from mycelium, the stability of protoplasts, their capacity for uptake of DNA, the regeneration of protoplasts into mycelium etc. Secondly, it is an additional requirement that the gene transfer and selection procedure should not affect the level of penicillin production.

The difficulties encountered in the development of transformant selection systems are also related to the limited knowledge of the genetic system of *P. chrysogenum*, which is difficult to study (e.g. because of the multinucleate nature of the filamentous mycelium and the absence of a sexual cycle, which only permits parasexual analysis (Pontecorvo et al., Adv. Genet. 5, 1953, 141–238)), the physical barriers which hinder the uptake of exogenous DNA (Peberdy, in: Biochemistry of Cell Walls and Membranes in Fungi; Kuhn, P. J., Trinci, A. P. J., Jung, M. J., Gossey, M. W., Copping, L. G. (eds) Springer-Verlag, Berlin 1989, 5–30) and the lack of DNA elements which allow for stable extra-chromosomal replication of the transforming DNA, which consequently results in very low transformation frequencies because the transforming DNA has to integrate into the genome of the host.

At this moment several systems for the selection of transformants have been described for *P. chrysogenum*. However, although the development of these selection systems has been useful in itself from a scientific point of view, the selection systems in current use suffer each from one or several of the following drawbacks which hinder their application to β-lactam producing industrial strains, particularly of *P. chrysogenum*.

Firstly, in some selection systems the phenotype selected for is conferred to *P. chrysogenum* by heterologous DNA (EP-A-240250; EP-A-215539; EP-A-225078; Cantoral et al., Bio/technology 5, 1987, 494–497; Beri and Turner, Curr. Genet. 11, 1987, 639–641; Kolar et al., Gene 62, 1988, 127–134; Stahl et al., App. Microbiol. Biotechnol. 26, 1987, 237–241; Picknett and Saunders, FEMS Microbiol. Lett. 60, 1989, 165–168; Whitehead et al., Mol. Gen. Genet. 216, 1989, 408–411). As a consequence of the public concern on recombinant DNA technology in general, the use of a transformant selection system for a β-lactam producing strain based upon a selection marker which consists of homologous DNA rather than heterologous DNA is preferred. Furthermore, from a practical point of view, transformation frequencies are usually higher when using homologous rather than heterologous selection markers.

Secondly, some selection systems depend on the generation of auxotrophic mutants of *P. chrysogenum* (EP-A-235951; EP-A-260762; Picknett et al., Curr. Genet. 12, 1987, 449–445; Diez et al., Curr. Genet. 12, 1987, 277–282). Generally spoken, the isolation of specific auxotrophic mutants requires extensive identification of mutant strains and is therefore rather time-consuming. This is a serious disadvantage when different hosts are used (e.g. in industrial strain improvement programs). In addition, and even more importantly, the introduction of auxotrophic mutations in industrial strains of *P. chrysogenum* often results in an unacceptable reduction of biosynthesis of penicillin. This phenomenon may be a consequence of the mutagenic treatment, necessary to introduce the required auxotrophic mutations in the strain of interest or may be related to particular auxotrophic defects per se (see for example 'O Sullivan and Pirt, J. Gen. Microbiol. 76, 1973, 65–75 and Stahl et al., ibid).

In *P. chrysogenum* breeding programs, aimed at the development of strains with increased penicillin production levels, the introduction of genetic markers, which require mutagenesis is therefore usually avoided (see for example Lein, In: Overproduction of Microbial Metabolites, Vanek, Z., Hostálek, Z. (eds), Butterworths, Boston, 1987, 105–140).

In conclusion, homologous selection systems which do not require mutagenesis of the host, like dominant selection systems or selection systems employing hosts which can be obtained by positive selection for a spontaneous mutation, are highly preferred. An example of the first category is the semi-dominant, homologous oliC selection system (EP-A-311272). However, a serious disadvantage of the oliC selection system is the very low frequency of transformation which limits the application of this selection system. An example of the second category is the niaD selection system which employs niaD mutants of *Penicillium chrysogenum*, obtained by positive selection for resistance to chlorate (Whitehead et al., ibid., AT patent application 8900266). Since resistance to chlorate can be obtained by spontaneous mutations at many different loci extra growth tests are necessary to identify the niaD mutants which form a drawback of this system. Another disadvantage of the niaD selection system is the observation that a large proportion of the *P. chrysogenum* transformants are genetically unstable (abortives), see Gouka et al., J. Biotechn. 20, 1991, 189–200.

Thirdly, for the application of recombinant DNA techniques in an industrial strain improvement program of β-lactam producing strains it is very important that a strain which has been transformed once can easily be transformed for a second time. Successive transformations have not shown to be possible in an efficient manner using the current selection systems. This feature is relevant as well for scientific studies on regulation of gene expression in *P. chrysogenum* and other filamentous fungi.

In summary, a convenient and reusable transformant selection system for *P. chrysogenum* based on the use of a homologous selection marker, suitable for application to industrial strains of a β-lactam producing micro-organism, particularly of *P. chrysogenum* is not available.

A system for the selection of transformants, particularly of a fungus, more particularly of a β-lactam producing strain of fungus, most particularly of *P. chrysogenum*, has now been developed which lacks the drawbacks of current selection systems. This selection system is based upon the complementation of fac, preferably facA mutants of β-lactam producing strains, particularly of *P. chrysogenum* (fac stands for fluoroacetate resistant) by transformation with the *P. chrysogenum* facA gene, encoding acetyl-CoA synthetase.

Recently, the facA gene of *A. nidulans* and the corresponding acu-5 gene of *N. crassa* have been isolated and characterized by nucleotide sequence analysis (Sandeman and Hynes, Mol. Gen. Genet. 218, 1989, 87–92; Thomas et al., Molec. Microbiol. 2, 1988, 599–606; Connerton et Al., Molec. Microbiol. 4, 1990, 451–460). The facA gene of the corn smut pathogen *Ustilago maydis* has also been isolated (Hargreaves and Turner, J. Gen. Microbiol. 135, 1989, 2675–2678). Fac mutants are phenotypically characterized by their inability to grow on acetate as a sole source of carbon. Therefore, Fac$^+$ transformants should be selectable for their regained capacity for acetate-utilization. However, the development of an efficient direct transformant selection system based on acetate-utilization appears to be difficult for *A. nidulans* and *N. crassa* (Ballance and Turner, Mol. Gen. Genet. 202, 1986, 271–275; Connerton et al, ibid) and *U. maydis* (Hargreaves and Turner, ibid).

The facA mutation can be selected for in *P. chrysogenum* with no need for mutagenic treatments like UV (ultra-violet) irradiation, exposure to chemical mutagens and the like. Spontaneous facA mutants, among others, can be isolated surprisingly efficiently by using a positive selection, for these mutants which are resistant to fluoroacetate. Stable facA mutants with very low reversion frequencies are readily obtained.

In *Aspergillus nidulans* and *Coprinus lagopus* mutations at three distinct genetic loci, termed facA, facB facC (Apirion, Nature 195, 1962, 959–961) and acu-1, acu-11, acu-12 (Casselton and Casselton, Mol. Gen. Genet. 132, 1974, 255–264) respectively, have been identified, each of them resulting in a fluoroacetate resistant, acetate non-utilizing phenotype. In addition to these fac/acu mutants, the same studies on *A. nidulans* and *C. lagopus* describe the isolation of a large number of fluoroacetate resistant but acetate-utilizing mutants, which are designated fanA, fanB, fanC, fanD and fanE in *A. nidulans* (Apirion, ibid). In contrast to this complex set of mutants the selection of facA mutants of *P. chrysogenum* is surprisingly efficient. Nearly all of the fluoroacetate resistant mutants of *P. chrysogenum* are acetate non-utilizers, mutated at the facA locus. A high proportion of these *P. chrysogenum* facA mutants have unaltered penicillin production characteristics as compared to the parent strain.

In the present invention a method for the efficient, direct selection of FacA$^+$ transformants of a β-lactam producing strain, particularly of *P. chrysogenum* on acetate containing medium is established by using the facA gene of *P. chrysogenum* as a homologous selection marker.

A homologous selection marker is defined in the present patent application as a selection marker derived from the species to which the transformant selection system is applied.

By the invention also the facA gene particularly isolated from *Penicillium chrysogenum* has been provided for. The invention also includes genes comprising different nucleotide sequences for instance with conservative mutations, where the sequence encodes the same amino acid sequence, but may have as many as 15% different bases, or mutations which are non-conservative, where fewer than about 10%, more usually fewer than about 5%, and preferably not more than 1% of the amino acids are substituted or deleted, and there are fewer than 5% of inserted amino acids, where the percent is based on the number of naturally occurring amino acids.

An additional advantage of the facA selection system over other selection systems is the rapid sporulation of acetate-utilizing colonies on acetate containing selection medium, which greatly improves and accelerates the transformant selection procedure. FacA$^+$ transformants are stable because the transforming DNA is integrated into the genome. The facA transformant selection system is suitable for the generation of different types of transformants, containing the transforming DNA integrated at the resident facA locus, at unknown genomic sites, in single and/or multiple copies. The generation of single-copy FacA$^+$ transformants by using circular, double-stranded DNA is surprisingly efficient. This feature allows for rapid isolation of facA mutants of the FacA$^+$ transformant and a repetition of the facA transformant selection procedure. This is another great advantage of the facA selection system.

The facA selection system can be applied to introduce non-selectable DNA into a host, preferably *P. chrysogenum*. The non-selectable DNA can be used to obtain or to enhance the production of a β-lactam compound in a host, preferably *P. chrysogenum*, for example by using non-selectable DNA like penicillin, cephalosporin or cephamycine biosynthetic genes (Veenstra et al., J. Biotechn. 17, 1991, 81–90, and Cantwell et al., Curr. Genet. 17, 1990, 213–221).

This invention provides a method to select transformants of a microorganism which has been transformed with DNA which method comprises:

isolating a mutant of the microorganism in which acetyl-CoA synthetase is inoperable or absent;

cotransforming said mutant with said DNA and an expression system effective in producing acetyl-CoA synthetase of *Penicillium chrysogenum;* and selecting transformants of said microorganism for ability to grow on a medium which contains a carbon source which requires acetyl-CoA synthetase activity for catabolism.

Furthermore, the invention provides a method for obtaining or enhancing the production of a β-lactam compound in transformants of a microorganism by applying the above-mentioned selection method which method comprises cotransforming said mutant with DNA encoding genetic information necessary for obtaining or enhancing the production of a β-lactam compound.

Preferably, the above-mentioned methods are applied homologously by using *Penicillium chrysogenum* transformed with the *P. chrysogenum* facA gene.

Finally the invention provides a gene entitled facA having the nucleotide sequence depicted in Sequence listing 1, particularly isolated from *P. chrysogenum*, and a vector and a host comprising the same. Also the facA gene wherein one or both of the expression signals has been replaced by other expression signals, obtained from the same or another organism has been provided together with a vector and a host comprising the same.

BRIEF DESCRIPTION OF THE FIGURES

FIG. 2: Southern blot analysis of PstI digested genomic DNA isolated from *P. chrysogenum* FacA$^+$ transformants by hybridization with (A) the 6.5 kb PstI fragment containing the facA gene of *P. chrysogenum* and (B) plasmid pPC1-1, for the detection of non-*P. chrysogenum* vector sequences in the transformants. The hybridizing band of approximately 7 kb in panel B is derived from hybridization of niaD sequences contained in pPC1-1 with the corresponding chromosomal niaD sequences. The intensity of this hybridization signal has been used as an internal standard for the amount of DNA loaded. The position of DNA size-markers is indicated p: pPC2-3; wt: *P. chrysogenum;* 1-14: different FacA$^+$ transformants.

BRIEF DESCRIPTION OF THE SEQUENCE LISTINGS

Figure 1:
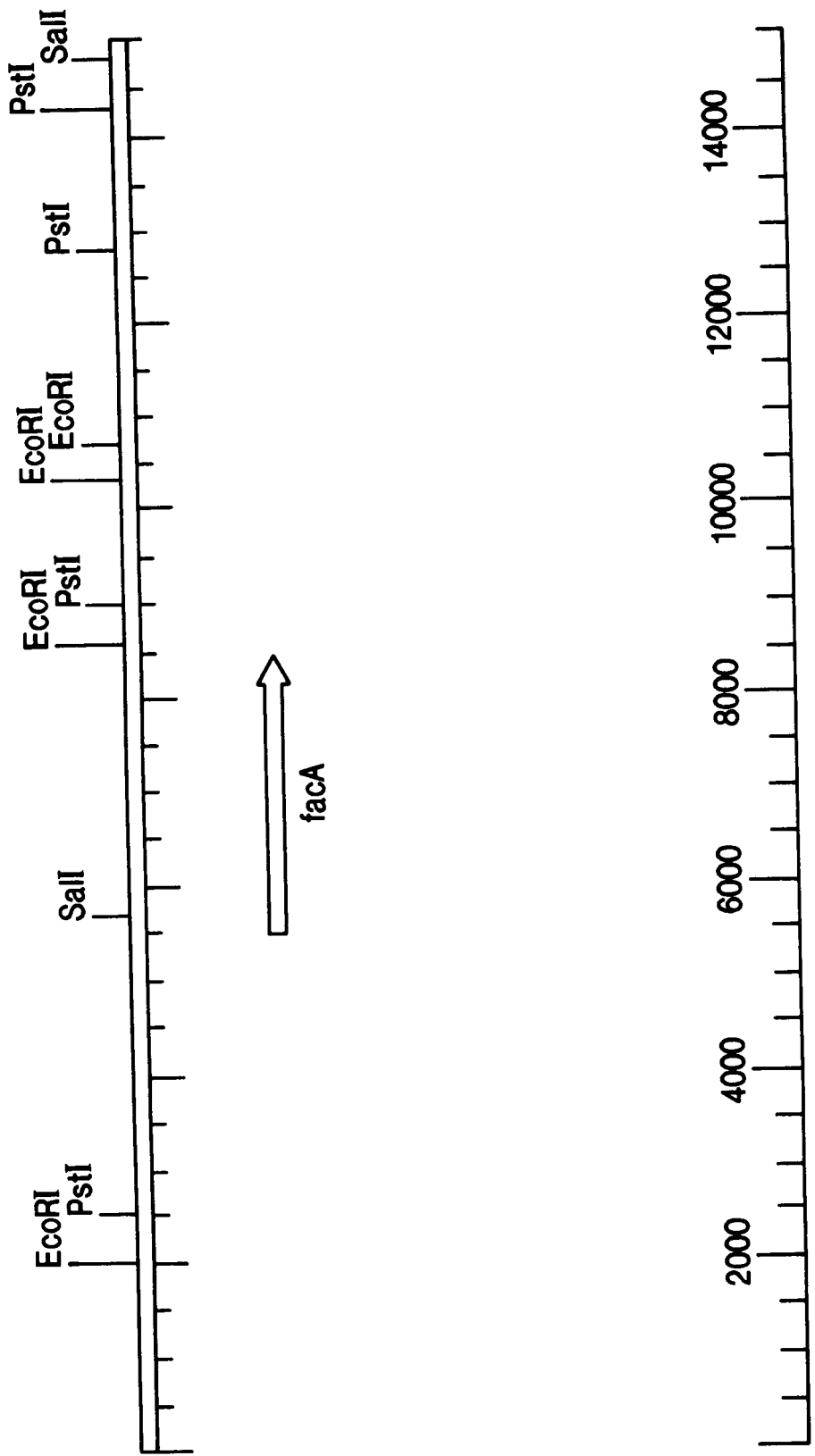
FIG. 1: Schematic representation of the *P. chrysogenum* DNA contained in lambda EMBL-3 phage facA7. The position and the direction of transcription of the facA gene is indicated (arrow). E: EcoRI, P: PstI, S: SalI.

Sequence listing 1: Nucleotide sequence of the facA gene of *P. chrysogenum* and derived sequence of amino acids.

Sequence listing 2: Amino acid sequence of acetyl CoA synthetase of *P. chrysogenum*.

Transformation of industrial strains of *Penicillium chrysogenum* by recombinant DNA can be achieved using methods well-known in the art (Peberdy, Mycol. Res. 93, 1989, 1–20). In a preferred embodiment of the invention, mycelium is harvested from a fresh culture and protoplasts are generated from the filamentous mycelium by enzymatic treatment, i.e. by Novozyme 234, in an osmotically stabilized medium. Then, DNA and protoplasts are mixed together in a $Ca^{2+}$ containing solution. Usually, several µg of DNA are added to $10^7$–$10^8$ protoplasts. Subsequently, polyethyleneglycol (PEG) is added to the mixture to mediate DNA uptake by the protoplasts. Finally, the protoplasts are plated onto an osmotically stabilized selection medium. Other techniques for the delivery of DNA into target cells have been described, i.e. transformation by electroporation (Richey et al., Phytopathology 79, 1989, 844–847), by biolistic™ (Du Pont Particle Delivery System) methods (Armaleo et al., Curr. Genet. 17, 1990, 97–103) or by liposome delivery systems (Felger and Holm, Focus 11, 1989, 21–25). The application of these techniques to filamentous fungi is still in its infancy, but in the scope of the invention the application of any chemical, physical or biological method for transformation of *P. chrysogenum* is envisaged.

Typical results obtained using the selection system described herein, are: 1) transformation frequencies, in the order of 1–100 transformants per µg of DNA, and 2) the observation that in all stable transformants the recombinant DNA is integrated into the genome. These results are typical for transformation systems of filamentous fungi (Rambosek and Leach, Critical Rev. Biotechn. 6, 1987, 357–393; Timberlake and Marshall, Science 244, 1989, 1313–1317; Peberdy, Mycol. Res. 93, 1989, 1–20).

As concerns the frequency of transformation, the possibility exists that the efficiency of the facA transformation procedure can be increased further by systematic variation of the reaction parameters in the transformation procedure, as has been described for example by Picknett for the trpC selection procedure (Picknett, British Thesis, DX 82490, British Library, Document Supply Centre, Boston Spa, Wetherby, UK). As concerns the nature of the integration event in the transformation process, it has been observed that transformation with double-stranded circular DNA results in three different types of integration of the vector: integration into unknown genomic sites ("type II" integration), into the resident facA locus ("type I" integration) and by gene-conversion or gene-replacement of the mutant allele ("type III" integration) (Rambosek and Leach, Critical Rev. Biotechn. 6, 1987, 357–393; Timberlake and Marshall, Science 244, 1989, 1313–1317).

Usually, some transformants contain multiple copies of the transforming DNA. These multiple copies are scattered throughout the genome or they are organised in a tandem array at a single locus. Typical multiple copy transformants contain both scattered and tandem integration patterns of transformed DNA. Sometimes, rearrangements have occurred in the transformed DNA. Although transformation by integration of the transforming DNA into the genome is the rule, it should be noted that stable transformants might also be obtained by stable extra-chromosomal maintenance of the transforming DNA. Such a situation of stable extra-chromosomal maintenance can be obtained when sequences necessary for autonomous replication (ars) and/or other sequences necessary for stable extra-chromosomal replication are part of the transforming DNA. These sequences might be added to the transforming DNA by conventional genetic-engineering techniques prior to the transformation process, or alternatively, it can be conceived that ars sequences are selected from the genome by in vivo integration and excision events during the transformation process (Powell and Kistler, J. of Bacteriol. 172, 1990, 3163–3171). It can be envisaged also that the transforming DNA is designed to function as an artificial chromosome in *Penicillium chrysogenum*, analogous to yeast artificial chromosomes (Burke et al., Science 236, 1987, 806–812) by the addition of centromere and telomere sequences, functional in *P. chrysogenum*, to the transforming DNA. Preferably, this invention relates to the stable transformation of *P. chrysogenum*, by stable integration of the transforming DNA into the genome of *P. chrysogenum*.

The transforming DNA, usually referred to as vector, typically consists of the following functional elements:

an origin of replication functional in *E. coli*, which is necessary for plasmid propagation in *E. coli*;

a selectable marker functional in *E. coli*, preferably not a β-lactamase gene, under control of appropriate *E. coli* expression signals, which is necessary for plasmid maintenance and transformant selection in E. coli;

a selectable marker functional in P. chrysogenum, preferably the facA gene of P. chrysogenum under control of appropriate P. chrysogenum expression signals, which is necessary for the selection of transformants in P. chrysogenum. Expression signals are defined herein as signals necessary and sufficient for efficient initiation and termination of transcription and efficient initiation and termination of translation. The selection marker is preferably expressed from its own, endogenous expression signals, although it is envisaged that appropiate expression of the marker might also be achieved by expression signals of other P. chrysogenum genes, e.g. the expression signals of the P. chrysogenum phosphoglycerate kinase (pgk) gene (Van Solingen et al., Nucl. Acid Res. 16, 1988, 11823) or orotidine-5'-phosphate decarboxylase (pyrG) gene, (EP-A-260762) or even by heterologous, non-P. chrysogenum expression signals obtained for instance from the A. nidulans glyceraldehyde-3-phosphate dehydrogenase (gpdA) gene (Punt et al., Gene 56, 1987, 117–124).

Optionally, the vector contains also the phage lambda cos sequence which is necessary for efficient in vitro packaging of the recombinant DNA into phage particles.

In another option, the vector contains also a sequence which acts to enhance the efficiency of transformation of P. chrysogenum, like the ans-1 sequence of A. nidulans (Ballance and Turner, Gene 36, 1985, 321–331; Cantoral et al., Bio/technology 5, 1987, 494–497) or the pyrG sequence of P. chrysogenum (EP-A-260762).

In yet another option, the vector contains one or more, non-selectable DNA sequences of interest.

Introduction of non-selectable DNA into P. chrysogenum occurs most efficiently when the non-selectable DNA is physically linked to a selectable marker. However, this linkage is not a prerequisite for transformation of non-selectable DNA. It is also possible to introduce non-selectable DNA and a selectable marker into P. chrysogenum by using distinct DNA molecules. Depending on the selection system used and on the molar ratio of distinct DNAs used for transformation, co-transformation frequencies obtained with distinct DNA molecules, range from a few % up to approximately 90% (see for example Kolar et al., Gene 62, 1988, 127–134). The present invention relates also to the application of co-transformation strategies of Penicillium chrysogenum with non-selectable DNA. Co-transformation. is defined in the present application as transformation of the selection marker together with non-selectable DNA which is physically linked or not to the selection marker, in the presence or absence of vector sequences. The non-selectable DNA is preferably derived from P. chrysogenum but it is envisaged that in the application of the invention the non-selectable DNA can be derived from a source other than P. chrysogenum. It should be noted that all sequences necessary for efficient manipulation, stable maintenance and replication of the vector in E. coli are not required for the selection of transformants of P. chrysogenum. Therefore, these sequences can be removed from the transforming DNA prior to transformation of P. chrysogenum, for instance by digestion with appropriate restriction enzymes and purification by gel-electrophoresis.

In a preferred embodiment of the invention the transforming DNA consists entirely of homologous, P. chrysogenum derived, sequences.

In another preferred embodiment of the invention the generation of stable transformants of P. chrysogenum is achieved by transformation of acetate non-utilizing industrial strains of P. chrysogenum. It is another preferred embodiment that acetate non-utilizing industrial strains of P. chrysogenum are obtained without mutagenesis, by positive selection for spontaneously resistance to fluoroacetate. The fluoroacetate resistant, acetate non-utilizing strains may be mutated at facA, facB or facC loci, analogous to the facA, facB and facC loci of A. nidulans and the acu-1, acu-11 and acu-12 loci of C. lagopus. In a still preferred embodiment of the invention the generation of stable transformants of P. chrysogenum is achieved by transformation of acetate non-utilizing industrial strains, mutated at the facA locus, with recombinant DNA containing the P. chrysogenum facA gene as a homologous selection marker.

In yet another preferred embodiment of the invention, transformants are assayed for complementation of the facA mutation by direct selection on medium containing acetate, although the possibility is recognized that other carbon sources like ethanol and the like which require acetyl CoA synthetase activity for catabolism might be used as well in the selection of FacA$^+$ transformants. A preferred embodiment of the invention is also the repeated application of the facA selection system to industrial strains of P. chrysogenum which have already been transformed using this selection system. The mutant facA genotype required for following transformation events, can be obtained by disruption or replacement of the wild type facA gene in the transformant by using the cloned facA gene of P. chrysogenum, but is preferably obtained by positive selection for spontaneous resistance to fluoroacetate.

The following non-limitative examples will illustrate the invention.

EXAMPLE 1

Isolation of Acetate Non-utilizing Mutants of P. chrysogenum

Positive selection for resistance to fluoroacetate has been used for the isolation of mutants of several strains of P. chrysogenum, one of them being P. chrysogenum strain P2 (ATCC 48271 (Lein, in: Overproduction of Microbial Metabolites, Vanek and Hostálek (eds) 1986, Butterworth Publishers, 105–139; Barredo et al., Curr. Genet. 16, 1989, 453–459)). These mutants are unable to utilize acetate as a carbon source. Approximately $10^6$–$10^7$ spores were plated onto 25 ml of solidified selective medium of the following composition (per 1000 ml, pH 6.5): glucose, 5 g; NaNO$_3$, 2 g; KCl, 1 g; KH$_2$PO$_4$.3H$_2$O, 3 g; MgSO$_4$.7H$_2$O, 0.5 g; fluoroacetate (Aldrich) 10 g and agar (Oxoid No 3), 15 g and 1 ml of a trace-element solution which contained per 1000 ml: ZnSO$_4$.7H$_2$O, 22 g; H$_3$BO$_3$, 11 g; MnCl$_2$.4H$_2$O, 5 g; FeSO$_4$.7H$_2$O, 5 g; CoCl$_2$.6H$_2$O, 1.7 g; CuSO$_4$.5H$_2$O, 1.6 g; Na$_2$MoO$_4$.2H$_2$O, 1.5 g; EDTA, 5 g.

Fluoroacetate resistant (fac) colonies were purified on selection medium and subsequently tested for their inability to grow on acetate medium. Acetate medium consisted of the minimal medium described above with the modification that potassium acetate, in a concentration of 100 mM, replaced glucose and fluoroacetate. All incubations were at 25° C.

Stable acetate non-utilizing mutants (reversion frequency $\leq 10^{-7}$, tested on acetate medium) were obtained for Penicillium chrysogenum at a frequency of approximately $1.10^{-6}$.

EXAMPLE 2

Acetyl-CoA Synthetase Activity in Acetate Non-utilizing Strains of P. chrysogenum Fluoroacetate resistant, acetate non-utilizing strains of P. chrysogenum P2 were further characterized biochemically by measurement of the acetyl-CoA synthetase activity. The strains were grown in shake flasks for 48 hours in a standard production medium, described in EP-A-357119. Then, the mycelium was harvested, lyophilized and ground in a mortar. Approximately, 0.4 g of ground mycelium was extracted for 45 minutes at 4° C. with 10 ml of a buffer containing Tris-HCl, 100 mM pH 7.3; EDTA, 0.4 mM; DTT, 0.1 mM and PMSF, 0.1 mM. Cell-free extracts were obtained by centrifugation of the extract for 25 minutes at 12.000 g. Acetyl-CoA synthetase activity was determined immediately after preparation of the cell-free extracts by measurement of acetate dependent depletion of CoA with Ellman reagent [5,5' dithio-bis-(2-nitrobenzoic acid)] (DTNB), basically according to procedures described by Takao (Takao et al., Agric. Biol. Chem. 51, 1987, 145–152). To 750 $\mu$l of mixture A, containing Tris-HCl (200 mM, pH 8.0), KCl (100 mM) and $MgCl_2$ (20 mM) 150 $\mu$l of mixture B, containing ATP (40 mM), LiCoA (15 mM) and acetate (20 mM) was added. The assay was started by the addition of 600 $\mu$l of cell-free extract to this mixture. The assay was performed at 30° C. At different time-intervals aliquots (150 $\mu$l) were removed from the reaction mixture. The aliquots were added to 100 $\mu$l of TCA (10% w/v). The solution was then neutralized with 100 $\mu$l of 0.6 N NaOH and buffered with 1.2 ml phosphate (0.2 M, pH 7.4). Subsequently, 100 $\mu$l of a DTNB solution (4 mg/ml in 0.2 M phosphate buffer, pH 7.4) was added. The extinction of the colour reaction was measured at 413 nm with a spectrophotometer (LKB) after centrifugation of the sample for 5 minutes at 3000 rpm (Heraeus labofuge M). Typical results, presented in Table 1, show that a large proportion of the acetate non-utilizer mutants are deficient in acetyl-CoA synthetase activity or have greatly reduced levels of this enzymatic activity.

TABLE 1

Relative activity of Acetyl-CoA synthetase in
P. chrysogenum P2 and some acetate non-utilizing
derivatives of P2 expressed in arbitrary units per mg
of protein per minute.

| Strain | | Acetyl-CoA synthetase activity (arbitrary units) |
|---|---|---|
| P2 | | 100 |
| P2-acetate non-utiliser | 1 | nd |
| | 2 | 14 |
| | 3 | 18 |
| | 4 | 10 |
| | 5 | nd | nd: not detectable.

EXAMPLE 3

Isolation and Characterization of the P. chrysogenum facA Gene

Chemically synthesized facA oligonucleotide probes were tested on Southern blots containing restriction enzyme digests of chromosomal DNA of P. chrysogenum P2 (not shown). Oligonucleotides were labelled at their 5' end using $\gamma$-[-$^{32}$P]-ATP and T4-polynucleotide kinase following standard procedures (Maniatis et al., in: Molecular Cloning, a laboratory manual, Cold Spring Harbor Laboratory, 1982 and 1989 (second edition)). The sequences of the oligonucleotides were derived from conserved regions in the nucleotide sequences of the A. nidulans facA gene any the homologous N. crassa acu-5 gene (Connerton et al., Molec. Microbiol. 4, 1990, 451–460). Hybridization and washing of the blots was performed at 56° C. using 6xSSC (0.9 M sodium chloride, 0.09 M sodium citrate) in the final wash.

Mixed probe facA7(5' GATGGCCCTC$_A^G$GGAAT-CATGGGAAGGTAGAT 3') generated a unique hybridization signal and was subsequently used for the screening of a genomic library of P. chrysogenum which has been made by methods well known in the art (Maniatis et al., ibid).

The facA gene of P. chrysogenum was isolated and characterized using standard procedures as described by Maniatis et al. (ibid).

DNA of some of the positively hybridizing phages has been purified. This DNA was further characterized by restriction enzyme analysis. The position of the facA gene on the cloned P. chrysogenum DNA in these phages has been determined by Southern blot analysis of restriction enzyme digests with facA specific oligonucleotide probes. In a control experiment, identical hybridizing fragments have been detected in chromosomal DNA of P. chrysogenum. By these means, the 6.5 kb PstI fragment present in phage facA7 (FIG. 1) has been identified as a suitable fragment for subcloning of the facA gene in the vector pBluescript® II (Stratagene, La Jolla). The resulting plasmid has been named pPC2-3.

The facA gene was further characterized by nucleotide sequence analysis, see Sequence listing 1. Comparison of this nucleotide sequence with the nucleotide sequences of the facA gene of A. nidulans revealed a 80% homology. The amino acid sequence of acetyl-CoA synthetase of P. chrysogenum deduced from the nucleotide sequence (Sequence listing 1 and 2) is 89% homologous (including conservative amino acid changes) to the sequence of the A. nidulans acetyl-CoA synthetase (Connerton et al., ibid). Homologies have been determined by using MicroGenie™ version 7.0 sequence analysis software (Beckman).

EXAMPLE 4

Transformation of Penicillium chrysogenum FacA Strains

P. chrysogenum facA strains were grown in 500 ml of a complete medium (YPD; 1% yeast extract, 2% peptone, 2% glucose) in a 2 l conical flask, by inoculating the medium with $2.10^6$ spores per ml and subsequent incubation for 18 hours in a rotating incubator at 25° C. and 300 rpm. After this incubation period, the mycelium was harvested by filtration of the medium through miracloth filtration wrap (Calbiochem). The mycelium was washed with 50 ml of sterile wash buffer containing 0.63 M NaCl and 0.27 M $CaCl_2$ in destilled water and excess buffer was removed by blotting the filter containing the mycelium between towels. The mycelium was weighed in a sterile tube and transferred to a 500 ml conical flask, to which 20 ml of a buffer (0.53 M Nacl, 0.27 M $CaCl_2$) containing 100 mg Novozym 234 (NOVO Nordisk) was added per gram mycelium. Protoplasts were allowed to form by incubation at 25° C. and gentle shaking (80 rpm) for 30–60 minutes, which process was followed microscopically. Free protoplasts were harvested by filtration of the suspension through glasswool, washing with an equal volume cold STC/0.63 M NaCl buffer (1.2 sorbitol, 10 mM Tris/pH 7.5, 50 mM $CaCl_2$) and subsequent centrifuging at 2500 rpm, 4° C. in 50 ml conical tubes using a swing-out rotor. The protoplasts were resuspended twice in 50 ml of STC/0.63 M NaCl buffer and centrifuged. Subsequently, the protoplasts were resuspended in a small volume of 0.7 M KCl buffer and the concentration of the protoplasts was determined using a haemocytometer. Finally, the protoplasts were diluted at a concentration of $10^8$/ml of STC/0.53 M NaCl and maintained on ice.

Aliquots of 100 µl of protoplasts suspension were added to sterile round bottom plastic tubes containing 10 µg linear or circular pPC2-3 DNA. After gentle mixing, the suspensions of protoplasts and DNA were incubated for 25 minutes at room temperature after which period a total volume of 1250 µl of a solution of polyethylene glycol (PEG) was added (60% PEG 4000 (BDH), 10 mM Tris/pH 7.5, 50 mM $CaCl_2$). The PEG solution was added as two aliquots of 200 µl, and one aliquot of 850 µl, with gentle but thorough mixing between each addition. This was followed by an incubation period of 20 minutes at room temperature. After incubation, the tubes were filled with 0.7 M KCl buffer and the protoplasts were spun down at 2500 rpm, 4° C. Subsequently, the protoplasts were plated on agar plates, containing 0.9 M KCl, 50 mM KAc, 0.001% glucose and minimal medium salts. The results of a typical experiment are given in Table 2. The vector pBluescript has been used as a negative control.

TABLE 2

Number of FacA+ transformants obtained with pPC2-3

| DNA | µg | No. of transformants |
| --- | --- | --- |
| pBluescript | 10 | 0 |
| pPC2-3 | 10 | 40 |

This result has been obtained by using various high-producing strains of *P. chrysogenum*, among them *P. chrysogenum* strain P2. It will be well known to those skilled in the art that the procedures for transformation require minor adjustments depending on the particular *P. chrysogenum* strain used.

Transformants usually sporulated within 7 days of incubation at 25° C. on the medium described above.

In pPC2-3 transformed strains acetyl-CoA synthetase activity (determined according to Example 2) was restored to or above wild type levels (Table 3).

TABLE 3

Relative activity of Acetyl-CoA synthetase in two FacA+ transformants and P2 expressed in arbitrary units per mg of protein per minute.

| Strain | | Acetyl-COA synthetase activity (arbitrary units) |
| --- | --- | --- |
| P2 | | 100 |
| FacA+ transformant | 1 | 200 |
| | 2 | 1000 |

EXAMPLE 5

DNA Analysis of Obtained Transformants

To verify the presence of intact vector sequences in the chromosomal DNA of the obtained FacA+ colonies and to identify transformants having only one copy of the vector integrated, DNA of 14 individual colonies was purified and analyzed by Southern hybridization. DNA of the colonies was isolated as follows. Complete medium as described in Example 4 (50 ml thereof in 250 ml conical flasks) was inoculated with $10^8$ spores of each colony, obtained after two cycles of single spore inoculations on minimal medium plates containing 100 mM KAc as sole carbon source. The medium was incubated at 300 rpm on a rotary shaker at 25° C. for 48 hours after which the mycelium was harvested using miracloth filtration wrap and washed with 25 ml of a 0.9% NaCl solution. Then the mycelium was weighed and frozen immediately in liquid nitrogen. Subsequently, portions of the mycelium were ground using a mortar and a pestle, while liquid nitrogen was added repeatedly, until a fine powder was obtained. The powder was added to a DNAse-free tube to which 10 ml of the extraction buffer was added per gram mycelium. The extraction buffer was prepared as follows: 40 ml of ice-cold 5xRNB buffer (1.0 M Tris-HCl, pH 8.5, 1.25 M NaCl, 0.25 M EDTA, autoclaved) was added to 80 ml of ice-cold p-aminosalicylic acid (123 g/l; Sigma) to which 80 ml ice-cold TNS (tri-isopropylnaphtalenesulfonic acid, sodium salt; 20 g/l; Eastman Kodak) was added. After mixing, a precipate was allowed to form on ice, from which the upper fluid was used for extraction of the mycelium.

After addition of the frozen mycelium powder to the extraction buffer the mycelium was allowed to thaw by vortexing and 0.5 volumes of phenol solution 1 was added immediately. Phenol solution 1 was prepared by dilution of phenol crystals in demineralized water and subsequent adjustment of the pH to 8.0 with NaOH solution. After addition of phenol solution 1, the mycelium suspension was mixed thoroughly and incubated on ice until the last mycelium sample was ground. Then, 0.5 volumes of chloroform was added to each tube and the tubes were mixed once again.

Next, the tubes were centrifuged at 12000 rpm, 4° C. for 10 minutes, using a swing-out rotor. The upper phases, containing the DNA, were transferred to new tubes to which 10 ml of phenol solution 2 was added. Phenol solution 2 was prepared by diluting 100 g phenol in 100 ml 25:1 (v/v) of chloroformisoamylalcohol. Then 1.6 mg of 8-hydroxyquinoline was added and the solution was saturated with STE (0.3 M NaCl, 10 mM Tris/pH 7.5, 0.1 mM EDTA).

After vortexing, the tubes containing the DNA were centrifuged once again and the upper phase transferred to another tube. Subsequently 3 volumes of 96% ethanol (stored at −20° C.) were added and the DNA was allowed to precipitate for 30 minutes at −70° C. The tubes were centrifuged at 20000 rpm for 15 minutes, 4° C. and the DNA pellets were washed with 70% ethanol (stored at −20° C.). The pellets were dried in a vacuum exsiccator for 3 minutes, resuspended in 0.5–1.0 ml of STE, depending on the size of the pellet, and transferred to eppendorf tubes. To each tube 10 µl of a 20 mg/ml RNAse A solution was added and the tubes were incubated for 15 minutes at 37° C. The DNA solutions were extracted again with phenol solution 2 for two or three times and the DNA was precipitated as described above. Finally, the washed pellets were dissolved in TE buffer (10 mM Tris/pH 7.5; 0.1 mM EDTA).

The procedure followed to analyse the chromosomal DNA by Southern hybridization was essentially carried out as described in Maniatis et al. (1982). DNA was digested with PstI, followed by separation of fragments on a 0.6% agarose gel and then transferred to nitrocellulose sheets. These blots were hybridized with either $^{32}$P labelled DNA of pPC1-1 or with the $^{32}$P labelled PstI fragment containing the *P. chrysogenum* facA gene (FIG. 2,A). Hybridization and washing of the blots was carried out at 65° C. using 0.2 x SSC in the final wash. After exposure of the blots to X-ray sensitive films the patterns of hybridization obtained were analyzed (FIG. 2,B). From this analysis it could be concluded that all but 2 transformants contain vector fragments. The pattern of these two transformants (Nos. 7 and 11) is indistinguishable of the wildtype pattern, which probably indicates that they arose after replacement or conversion of the mutant allele. Six transformants (Nos. 1, 2, 3, 6, 10 and 12) contain a single copy of the vector at the resident facA locus whereas four (Nos. 4, 8, 13 and 14) contain a single vector copy at an unknown genomic site. Two transformants (Nos. 5 and 9) contain multiple copies of the vector. This experiment demonstrated that the facA transformant selection system is a versatile selection system, suitable for different applications like for example the generation of single-copy transformants, the generation of multi-copy transformants, integration at the resident facA locus, or integration at unknown genomic sites.

EXAMPLE 6

Penicillin Production of FacA Mutants of *P. chrysogenum*

The effect of the fluoroacetate selection procedure on penicillin production has been determined for 3 stable facA mutants, obtained from approximately $3.10^6$ spores as has been described in Example 1. The production of penicillin was determined in shake flask experiments, in two independent experiments, using procedures which have been described before in EPA-357119. The results are summarized in Table 4.

TABLE 4

Penicillin production of facA mutants of *Penicillium chrysogenum*. The amount of penicillin is expressed in arbitrary units. The number of arbitrary units produced by P2 is arbitrarily set at 100.

| Strain | Penicillin production (arbitrary units) |
|---|---|
| P2 | 100 |
| P2 facA1 | 103 |
| P2 faaA5 | 91 |
| P2 facA7 | 109 |

This experiment shows that facA mutants with unaltered penicillin production characteristics are readily obtained. FacA$^+$ transformants with unchanged levels of penicillin production compared to the parent strain P2 were also readily obtained by transformation of the facA mutants with pPC2-3 (not shown).

EXAMPLE 7

Repeated Use of the FacA Transformation System

A *P. chrysogenum* facA strain was transformed with pPC2-3. Transformants containing a single copy of the transforming facA gene were identified, as has been described in Example 5. Such a transformant was subjected to a second round of (1) selection for acetate non-utilising facA mutants and (2) a second transformation with pPC2-3 as has been described in Example 4. Acetate non-utilizing mutants were obtained by positive selection on minimal medium containing fluoroacetate as has been described in Example 1. The frequency of occurrence of fluoroacetate resistant, acetate non-utilizing colonies was comparable to the frequency observed with the parent strain P2.

Second generation facA mutants, identified as has been described in Example 2, behaved in a similar way in transformation experiments, in stability tests and in penicillin production tests as has been described for first generation facA mutants (see Examples 4, 5 and 6). The experiments described here demonstrate that efficient repeated application of the facA transformation system is possible.

EXAMPLE 8

Homologous Transformation

The feasibility of complete homologous transformation by using the 6.5 kb Pst I restriction fragment of pPC2-3 is demonstrated.

Plasmid pPC2-3 was propagated by using *E. coli* strain JM109 (Yanish-Perron et al., Gene 33, 1985, 103–109) and purified according to methods well known in the art (Maniatis et al., ibid.). The purified plasmid pPC2-3 was then digested with restriction enzyme Pst I (New England Biolabs) to liberate the *P. chrysogenum* derived sequences from pBluescript vector sequences. The fragment containing the *P. chrysogenum* derived sequences, 6.5 kb in length, was purified from pBluescript vector sequences by agarose gel electrophoresis followed by electroelution from the agarose gel (Bio-trap™, Schleicher and Schuell).

The purified 6.5 kb Pst I restriction fragment was then used for transformation of facA strains of *P. chrysogenum* according to procedures described in Example 4. Transformation frequencies were similar to those obtained by using the entire plasmid pPC2-3 (Table 5).

TABLE 5

| DNA | μg | No. of transformants |
|---|---|---|
| pBluescript | 10 | — |
| pPC2-3 | 10 | 40 |
| 6.5 kb Pst I fragment | 10 | 50 |

Number of FacA$^+$ transformants

The absence of pBluescript vector sequences were subsequently demonstrated by using a sensitive colony-hybridization procedure (Kinsey, Fungal Genetics, Newslett. 36, 1989, 45–47) and by using randomly labeled pBluescript as a probe (Maniatis et al., ibid.).

EXAMPLE 9

FacA Mediated Co-transformation

The possiblity to introduce non-selectable DNA into *P. chrysogenum* by using the facA selection system is demonstrated the control experiment described in this example.

A *P. chrysogenum* facA mutant was transformed with the 6.5 PstI restriction fragment as described in example 8 together with a 3 kb *P. chrysogenum* derived SalI restriction fragment which contains an oligomycine resistant oliC gene. Such an oliC gene can be obtained from *P. chrysogenum* by methods described in detail (Bull et al., Curr. Genet. 1988, 13, 377–382).

Transformants were selected first for growth on acetate containing medium as described in Example 4. Then, following purification of transformants on acetate medium, transformants were tested for resistence to oligomycine by growth on solid medium containing 3 μg/ml oligomycine (Sigma). Oligomycin resistant transformants were readily obtained using a 1:1 molar ratio of facA/oliC DNAs.

From these results it is concluded that co-transformation readily occurs by using the facA selection system. Physical linkage of the selection marker to the non-selectable DNA is not required for co-transformation.

EXAMPLE 10

Selection on Ethanol Containing Media

The possibility to select FacA$^+$ transformants on medium containing ethanol rather than acetate as a carbon source is demonstrated. FacA⁺ transformants were obtained by procedures described in Example 4. The transformation mixture was plated on selection medium containing 0.1%, 0.3% or 1% ethanol instead of 50 mM potassium acetate. Otherwise, the selection medium used in this example is identical to the medium described in Example 4.

After approximately 2–3 weeks of incubation at 25° C. transformants could clearly be identified. By using ethanol containing selection medium the frequency of transformation was reduced to approximately 0.5–1 transformants/µg of DNA.

This example demonstrates the feasibility to use other carbon sources than acetate, which require acetyl-CoA synthetase activity for catabolism.

We claim:

1. A method to select a transformed strain of the genus Penicillium, Aspergillus, or Acremonium which has been transformed with a first DNA of interest which method comprises:

cotransforming a first mutant strain of said Penicillium, Aspergillus, or Acremonium which first mutant strain contains an inoperable facA gene and is unable to utilize acetate, with said first DNA of interest and with a selection marker DNA comprising an expression system effective in producing the acetyl CoA synthetase encoded by a fungal facA gene; and directly selecting first transformed strains for ability to grow on acetate-containing medium.

2. The method of claim 1 wherein at least some of said first transformed strains can be mutated to contain an inoperable facA gene and selected for said mutation to obtain a second mutant strain that contains an inoperable facA gene and is unable to utilize acetate.

3. The method of claim 1 wherein said cotransforming is conducted by supplying said first DNA of interest and said selectable marker DNA comprising said expression system on the same DNA molecule.

4. The method of claim 1 wherein the fungal acetyl CoA synthetase is homologous to the acetyl CoA synthetase of said first mutant strain.

5. The method of claim 1 wherein said first mutant strain is from the genus Penicillium.

6. The method of claim 1 where said first mutant strain is from the genus Aspergillus.

7. The method of claim 1 where said first mutant strain is from the genus Acremonium.

8. The method of claim 1 wherein said first mutant strain is selected from the group consisting of *Penicillium chrysogenum, Aspergillus nidulans* and *Acremonium chrysogenum.*

9. The method of claim 8 where said first mutant strain is *P. chrysogenum.*

10. The method of claim 8 where said first mutant strain is *A. nidulans.*

11. The method of claim 8 where said first mutant strain is *A. chrysogenum.*

12. The method of claim 4 wherein said first mutant strain is from the genus Penicillium.

13. The method of claim 4 where said first mutant strain is from the genus Aspergillus.

14. The method of claim 4 where said first mutant strain is from the genus Acremonium.

15. The method of claim 1 wherein said first mutant strain is a β-lactam producing strain.

16. The method of claim 2 which further includes selecting said second mutant strain.

17. The method of claim 16 wherein said second mutant strain is selected by fluoroacetate resistance.

18. The method of claim 17 which further includes cotransforming said second mutant strain with a second DNA of interest and with a selection marker DNA comprising an expression system effective in producing the acetyl CoA synthetase encoded by a fungal facA gene.

19. The method of claim 18 which further includes selecting second transformants of said second mutant strain for ability to grow on acetate-containing medium.

20. A method to select a transformed strain of a β-lactam producing fungus which has been transformed with a first DNA of interest which method comprises:

cotransforming a first mutant strain of said β-lactam producing fungus which first mutant strain contains an inoperable facA gene and is unable to utilize acetate, with said first DNA of interest and with a selection marker DNA comprising an expression system effective in producing the acetyl CoA synthetase encoded by a fungal facA gene; and directly selecting first transformed strains for ability to grow on acetate-containing medium.

21. The method of claim 20 wherein at least some of said first transformants can be mutated to contain an inoperable facA gene and selected for said mutation to obtain a second mutant strain that contains an inoperable facA gene and is unable to utilize acetate.

22. The method of claim 20 wherein said cotransforming is conducted by supplying said first DNA of interest and said selectable marker DNA comprising said expression system on the same DNA molecule.

23. The method of claim 20 wherein the acetyl CoA synthetase is homologous to the acetyl CoA synthetase of said first mutant strain.

24. The method of claim 21 which further includes selecting said second mutant strain.

25. The method of claim 24 wherein said second mutant strain is selected by fluoroacetate resistance.

26. The method of claim 24 which further includes cotransforming said second mutant strain with a second DNA of interest and with a selection marker DNA comprising an expression system effective in producing the acetyl CoA synthetase encoded by a fungal facA gene.

27. The method of claim 26 which further includes selecting second transformants of said second mutant strain for ability to grow on acetate-containing medium.

* * * * *